United States Patent [19]

Mauck

[11] Patent Number: 5,032,504
[45] Date of Patent: Jul. 16, 1991

[54] DIAGNOSTIC TEST KIT AND METHOD FOR DETERMINATION OF CHLAMYDIAL OR GONOCOCCAL ANTIGENS USING A MICROPOROUS MEMBRANE

[75] Inventor: John C. Mauck, Rochester, N.Y.

[73] Assignee: Eastman Kodak Company, Rochester, N.Y.

[21] Appl. No.: 255,920

[22] Filed: Oct. 7, 1988

[51] Int. Cl.$^5$ .................. C12Q 1/00; G01N 33/53
[52] U.S. Cl. ............................ 435/7.36; 435/28; 435/871; 436/510; 436/511
[58] Field of Search .......... 436/510, 511, 518, 531, 436/808, 810, 823; 435/7, 805, 810, 871, 7.36

[56] References Cited

U.S. PATENT DOCUMENTS

| 4,241,045 | 12/1980 | Gaafar . |
| 4,340,479 | 7/1982 | Pall . |
| 4,497,899 | 2/1985 | Armstrong et al. . |
| 4,497,900 | 2/1985 | Abram et al. . |
| 4,695,537 | 9/1987 | Dorsett .................. 435/7.36 |
| 4,810,630 | 3/1989 | Craig ........................ 435/7 |
| 4,828,983 | 5/1989 | McClune .................. 435/14 |
| 4,830,960 | 5/1989 | Appleton ................ 436/518 |
| 4,874,691 | 10/1989 | Chandler .................. 436/535 |

FOREIGN PATENT DOCUMENTS

| 0173500 | 3/1986 | European Pat. Off. . |
| 0264036 | 4/1988 | European Pat. Off. . |
| 187862 | of 1983 | Japan . |

OTHER PUBLICATIONS

U.S. Ser. No. 255,923 filed Oct. 7, 1988 by Pronovost.
Pall Corp. trade literature PSD-750a, Mar. 1983, pp. 1-20.
Pall Corp. trade literature: "Product Information", pp. 1-3, Dec., 1986.
Batteiger et al., The Use of Tween 20 as Blocking Agent in Immunological Detection, Journal of Immun. Methods, 55(1982), 297-307.

Primary Examiner—Sam Rosen
Attorney, Agent, or Firm—J. Lanny Tucker

[57] ABSTRACT

Antigens from chlamydial or gonococcal organisms in specimens containing whole blood, mucus or components thereof can be rapidly and sensitively determined using a polyamide microporous membrane which is coated with a surfactant. This determination is accomplished by contacting extracted antigen with the coated polyamide microporous membrane which is substantially free of any particulate matter. The membrane has an average pore size of from about 1 to about 10 $\mu$meter. Within about 10 minutes of that contacting, antigen bound to the coated membrane is contacted with chlamydial or gonococcal antibody, respectively, so as to form an immunological complex on the membrane. The presence of the complex on the membrane is then determined as a measure of the amount of chlamydial or gonococcal antigen present in the specimen.

20 Claims, No Drawings

DIAGNOSTIC TEST KIT AND METHOD FOR DETERMINATION OF CHLAMYDIAL OR GONOCOCCAL ANTIGENS USING A MICROPOROUS MEMBRANE

FIELD OF THE INVENTION

The present invention relates to a surfactant-coated membrane, diagnostic kit and method for the detection of chlamydial or gonococcal organisms in a biological specimen. More particularly, it relates to the detection of such antigens in specimens which contain whole blood, mucus or components thereof.

BACKGROUND OF THE INVENTION

Immunoassays have been used in recent years to detect the presence of infectious diseases. In order for the assay to be useful, it must detect a particular organism with a high degree of reliability. In most cases, this requires the isolation and reaction of antigens peculiar to the organism with corresponding antibodies. For the test to be commercially successful, it also needs to be relatively inexpensive, simple to use and rapid.

One such organism which can be detected by immunoassay is *Chlamydia trachomatis* (herein *C. trachomatis*) which is one of two microbial species of the genus Chlamydiaceae, order Chlamydiales. There are 15 or more strains of this species which are the causes of a number of human ocular and genital diseases including trachoma, inclusion conjunctivitis, lymphogranuloma venereum, nongonococcal urethritis and proctitis. Infection from *C. trachomatis* is pervasive in the general population so that it is believed that there are millions of cases each year of nongonococcal urethritis alone.

Gonorrhea is a disease usually transmitted by sexual contact caused by a bacterium of the Neisseria genus, especially *N. gonorrhoeae*. The disease has plagued mankind for thousands of years, and although antibiotics have helped control its spread, it still persists in epidemic proportions in many parts of the world. The importance of detection and treatment of this organism is well recognized. *N. meningitidis* and *N. lactamica* are also species of considerable medical and diagnostic interest.

Because of the widespread nature of these diseases, there is considerable interest in having a rapid, simple and reliable test for detection of chlamydial and gonococcal organisms. Considerable research has been carried out to find useful ways to extract detectable antigen from chlamydial organisms. See for example, U.S. Pat. Nos. 4,427,782 (issued Jan. 24, 1984 to Caldwell et al) and 4,663,291 (issued May 5, 1987 to Rose) and E.P. Publications Nos. 174,106 (Becton) and 193,431 (Caldwell et al).

Assays for *C. trachomatis* and *N. gonorrhoeae* carried out using a solid support are described in U.S. Pat. Nos. 4,497,899 and 4,497,900, respectively (both issued Feb. 5, 1985 to Armstrong et al and Abram et al, respectively). The described assays are performed by extracting antigen from the organism and coating it on a bare solid support. The coated antigen is then detected with either one or two antibodies, one of which is suitably labeled. The critical feature of the assays appears to be the use of a solid support for attachment which is untreated or uncoated with any material. Attachment of antigen is apparently achieved by incubating the coated support for an extended time sufficient to cause adsorption of antigen thereon (Col. 2, lines 51-55 of U.S. Pat. No. 4,497,899). From the examples of this patent, this time is determined to be at least 30 minutes at elevated temperature (37° C.). The entire assay described in U.S. Pat. No. 4,497,899 takes at least 3 hours to perform. A similar but somewhat quicker assay is described in U.S. Pat. No. 4,497,900 for *N. gonorrhoeae* (see Cols. 4 and 5).

It would be desirable to have a much more rapid test for chlamydial or gonococcal organisms which has high reliability and can be performed at room temperature. Such an improvement is described and claimed in copending U.S. Ser. No. 255,923, filed on even date herewith by Pronovost and entitled "Determination of a Chlamydial or Gonococcal Antigen Using a Positively-Charged Ionically Binding Support". My colleague found that ionically charged supports attract chlamydial or gonococcal antigen and enable one to quickly and sensitively detect such antigens. However, I have found that with some biological specimens, especially those containing copious amounts of whole blood, mucus or components thereof, that assays using the ionically charged microporous membranes can be further improved.

Thus, while the Pronovost application describes a remarkable advance in the diagnostic art, further improvements are needed.

SUMMARY OF THE INVENTION

The problems noted above are overcome with a method for the determination of a chlamydial or gonococcal antigen comprising:

A. contacting chlamydial or gonococcal antigen extracted from a specimen suspected of containing chlamydial or gonococcal organisms, respectively, the specimen further containing whole blood, mucus or components thereof, with a surfactant-coated polyamide microporous membrane which is substantially free of any particulate matter, and which has an average pore size of from about 1 to about 10 $\mu$meter, the surfactant coating being present in an amount of at least about 20 mg/m$^2$, B. within about 10 minutes of contacting step A, contacting chlamydial or gonococcal antigen bound to the coated membrane with chlamydial or gonococcal antibody, respectively, so as to form an immunological complex on the membrane, and C. determining the presence of the complex on the membrane as a measure of the presence of chlamydial or gonococcal antigen, respectively, in the specimen.

The membrane useful in the method described above is coated with a surfactant in an amount of at least about 20 mg/m$^2$. This coated membrane can be supplied for the method as a part of a diagnostic test kit further comprising a reagent composition test kit further comprising a reagent composition comprising the chlamydial or gonococcal antibodies used in the method.

The assay of this invention is rapid, reliable and simple to use. For example, it can be carried out in less than 30 minutes at room temperature. It is highly reliable for detecting extracted chlamydial antigen (such as from *C. trachomatis*), and particularly the lipopolysaccharide antigen. It can also be used to rapidly and sensitively detect gonococcal antigens (such as proteins IA and IB from *N. gonorrhoeae*). These advantages are achieved with the invention described and claimed in U.S. Ser. No. 255,923 of Pronovost (noted above).

However, the present invention achieves additional advantages because it enables one to carry out the assay of biological specimens which may contain whole blood, mucus or components thereof. Such materials sometimes clog microporous membranes which have ionic charges, and drastically slow down the assay. It is uncertain as to what causes the clogging by some specimens and not others.

However, it is clear that commercial assays must be rapid and capable of processing specimens no matter what material may be present. The present invention is such an assay. It is carried out with a polyamide microporous membrane having an average pore size of from about 1 to about 10 μmeter. The membrane is substantially free of any particulate material which may be used for antigen capture, and is coated with a a certain amount of a surfactant. The present invention can be carried out at room temperature with minimal equipment and technical skill.

DETAILED DESCRIPTION OF THE INVENTION

The present invention comprises a method for determining the presence of *C. trachomatis* (or other chlamydial species), or the presence of *N. gonorrhoeae* (or other gonococcal species) in a biological specimen which has been obtained from a patient using any suitable medical or diagnostic techniques. Such specimens include, for example, swab specimens obtained from the cervix, urethra, throat or anus of a patient, and body fluids such as synovial fluid or fluid from lesions. The biological specimens so obtained are suspected of containing bacterial organisms which comprise the chlamydial or gonococcal antigen (or mixture thereof) to be determined. The specimens are particularly likely to contains whole blood or mucus, and sometimes large amounts of both.

While the assay can be carried out to detect antigens from intact chlamydial or gonococcal organisms, it is usually desirable to extract the antigens from the organisms in order to increase assay sensitivity. Standard techniques can be used for lysing the organism to release antigen including, for example, solvent dilution or high pH lysing solutions, enzyme treatment and physical agitation such as sonication or centrifugation. Heating is described as a lysing technique in E.P. Publication No. 183,383 (published June 4, 1986). The use of anionic detergents or salts such as sodium dodecyl sulfate and deoxycholate is described in U.S. Pat. Nos. 4,497,899, 4,497,900 (both noted above) and 4,663,291 (issued May 5, 1987 to Rose).

In a preferred embodiment, the present invention can be used to detect the chlamydial lipopolysaccharide (glycolipid group) antigen (as described, for example, in E.P. Publication No. 193,431, published Sept. 3, 1986). Extraction procedures are also described therein. In another embodiment, the detected antigen can be the chlamydial major outer membrane protein of the organism which comprises about 60% of the total associated outer membrane protein. This antigen and methods of extraction are described in U.S. Pat. No. 4,427,782 (issued Jan. 24, 1984 to Caldwell et al). In some instances, a mixture of these chlamydial antigens will be detected using the present invention. In still other embodiments, the invention is used to detect one or more gonococcal antigens (IA or IB protein), or mixtures of antigens from individual gonococcal strains.

A preferred extraction composition is described in detail in copending U.S. Ser. No. 255,928 filed on even date herewith by Pronovost, Mauck, Sullivan, Greer and Gilbert and entitled "High pH Extraction Composition and Its Use to Determine a Chlamydial, Gonococcal or Herpes Antigen". The central feature of that composition is the presence of an alcoholamine or salt thereof and its high pH. Further details of this preferred composition are provided below in relation to the examples.

In addition, it may be desirable to use a protease in the extraction procedure to break down whole blood and mucus. This is described in copending U.S. Ser. No. 255,922 filed on even date herewith by Gilbert, Mauck and Stowers and entitled "Use of a Protease in the Extraction of Chlamydial, Gonococcal and Herpes Antigens".

Once antigen is extracted from the organism, it is desirable, although not essential, that the specimen be prefiltered to remove cell debris, particulate matter and other unwanted materials prior to further handling. Prefiltering can be carried out in a suitable container having a filter of some type. While prefiltering may be carried out, it does not always remove all of the extraneous materials so as to facilitate the assay. Thus, the present invention overcomes the failures of any prefiltering after extraction.

Extraction can be carried out in any suitable container, including devices specially designed for extraction of antigen. Useful devices are known in the art, including U.S. Pat. No. 4,746,614 (issued May 24, 1988 to Devaney, Jr. et al).

Extracted antigen is contacted with a polymeric microporous membrane having an average pore size of from about 1 to about 10 μmeter, and preferably of about 5 μmeter. The membrane is prepared from a polyamide, that is a long-chain synthetic polymer having recurring amide groups in the polymer backbone. They are generally copolymers of a diamine and a dicarboxylic acid, or homopolymers of a lactam of an amino acid. Representative materials include, but are not limited to, polyhexamethylene dodecanediamide (nylon 612), polyhexamethylene adipamide (nylon 66), poly-ε-caprolactam (nylon 6), polyhexamethylene sebacamide (nylon 610) and poly-7-aminoheptanoamide (nylon 7), and mixtures thereof. Polyhexamethylene adipamide (nylon 66) is preferred.

Further details of useful membrane materials and details of their preparation are found in various published references including U.S. Pat. No. 4,340,479 (issued July 20, 1982 to Pall) and Pall Corp. trade literature brochures PSD-750a (March, 1983, pp. 1–20) and NM-900c (September, 1984, pp. 1–28). A preferred polyamide microporous membrane is the nylon 66 membrane manufactured and sold by Pall Corp. as Biodyne®-A membrane.

The membrane is substantially free of particulate material, such as polymeric particles, which may be used for antigen capture, for example as described in E.P. Publication No. 264,036 (published Apr. 20, 1988).

In the practice of this invention, the membrane is coated or treated with one or more surfactants in an amount of at least about 20, and preferably from about 50 to about 150, mg/m². Useful surfactants include, but are not limited to, anionic, amphoteric or nonionic surfactants, with nonionic surfactants being preferred. There are many useful surfactants, and a worker skilled in the art can consult the standard resource, *McCutch-* eon's *Emulsifiers and Detergents*, 1986 Ed., McCutcheon Division Publishing Co., Glen Rock, N.J. to find useful surfactants. For example, useful anionic surfactants include, but are not limited to sodium dodecyl sulfate, lithium decyl sulfate, ammonium dodecyl sulfate, sodium decyl sulfate and others known in the art. Useful amphoteric surfactants include Zonyl TM FSK and others known in the art.

Particularly useful nonionic surfactants include fluorinated nonionic surfactants such as perfluoroalkyl-poly(ethylene oxide) alcohols, for example commercially available as Zonyl TM FSN (DuPont), Nonidet P-40 (Sigma Chemical) or as Fluowet TM OT (American Hoechst).

Coating the membrane with a surfactant or mixture thereof can be accomplished in any suitable way, for example, by dipping the membrane in a solution (aqueous or organic) of the surfactant, or by applying the surfactant by a coating technique. Once coated, the membrane is dried under suitable conditions.

The surfactant-coated membrane described herein can be used in combination with other equipment (bottles, test tubes, swabs, beakers or cups) in order carry out the assay. Alternatively and preferably, it is fitted into a disposable test device in which the assay can be carried out and all fluids accommodated. Useful configurations of test devices are known in the art including U.S. Pat. Nos. 3,825,410 (issued July 23, 1974 to Bagshawe), 3,888,629 (issued June 10, 1975 to Bagshawe), 3,970,429 (issued July 20, 1976 to Updike) and 4,446,232 (issued May, 1984 to Liotta). Particularly useful devices are described and claimed in copending and commonly assigned U.S. Ser. Nos. 19,810 (filed Feb. 27, 1987 by Hinckley) and 98,248 (filed Sept. 18, 1987 by Hinckley).

Almost immediately upon contact of the antigen with the coated membrane, the antigen is bound thereto. The antigen is preferentially bound to the membrane as opposed to other proteins, cell components, whole blood or mucus or other debris which may be present in the test specimen or reagents used in the assay.

Within about 10 minutes, and preferably within 1 to 5 minutes, of the contact, the bound antigen is contacted with a reactive composition comprising a chlamydial or gonococcal antibody so as to form an immunological complex bound to the support. Fluid and unbound materials may be removed quickly at the same time. If the assay is carried out using a disposable test device, fluid and unbound materials (such as whole blood and mucus components) in the specimen are allowed to flow through the membrane and collected in a suitable compartment during the time the antigen is bound to the membrane.

The antibody used in this assay is specifically immunoreactive with one or more chlamydial or gonococcal strains (depending upon what organism is of interest). It can be polyclonal or monoclonal. If polyclonal, it is commercially available or prepared in various animals using known techniques employing an antigen common to the strain of organism to be detected. A single antibody or mixture thereof can be used. For example, antibody to either the chlamydial lipopolysaccharide or major outer membrane protein antigen, or antibodies to both antigens can be used in the assay. Preferably, the antibodies are monoclonal which are either commercially available or prepared using standard hybridoma technology. Useful procedures for preparing antibodies are described, for example, in E.P. Publication No. 193,431 and U.S. Pat. No. 4,427,782 (noted above).

In one embodiment, the antibody to the antigen is labeled for detection. Useful labels are known in the art and include chemical or biological compounds which are directly detectable using suitable procedures and equipment, as well as compounds which can be detected through further chemical or specific binding reactions to provide a detectable species. Examples of useful labels include radioisotopes, enzymes, fluorescent compounds, chemiluminescent compounds, phosphorescent compounds, biotin or its derivatives, avidin or its derivative, ferritin, magnetizable particles, dyed particles, gold sols, dye sols, colored *Staphylococcus aureus* cells and others readily apparent to one skilled in the art. Radioisotopes or enzymes are preferred labels. The labels can be attached to antibodies using known techniques. Where the label is not directly detectable, further reagents or compounds are needed to render the reaction or specific binding product detectable. For example, if the label is biotin, it can be reacted with avidin which is conjugated with an enzyme to provide a detectable species. Where the label is an enzyme, such as glucose oxidase, urease, peroxidase, alkaline phosphatase and others, substrates in dye-providing compositions are also needed.

In a particularly preferred embodiment, the label is peroxidase, and at some point in the assay, hydrogen peroxide and a suitable dye-providing composition is added to provide a detectable dye. For example, useful dye-providing reagents include leuco dyes, such as triarylimidazole leuco dyes (as described in U.S. Pat. Nos. 4,089,747, issued May 16, 1978 to Bruschi), or other compounds which react to provide a dye in the presence of peroxidase and hydrogen peroxide (that is, compounds which react to provide a dye upon catalytic action of peroxidase).

In a preferred embodiment, the chlamydial or gonococcal antibody is not labeled, and detection of the antibody-antigen complex formed and bound to the membrane is accomplished using a second antibody (described below) which is specific to the unlabeled antibody and is appropriately labeled.

The chlamydial or gonococcal antibody can be contacted with the bound antigen in a reagent composition (also known as a blocking composition) further comprising one or more proteins which reduce nonspecific interactions on the support. Useful proteins are well known and include, for example, casein, α-casein, fetal bovine serum and porcine gamma globulin. A particularly useful reagent composition comprises a protein and an amphoteric surfactant, as described and claimed in copending U.S. Ser. No. 255,925 filed on even date herewith by Pronovost and entitled "Immunological Reagent Composition and Its Use in the Determination of Chlamydial or Gonococcal Antigens."

Once the bound antigen has been contacted with the chlamydial or gonococcal antibody, a bound immunological complex is formed on the coated membrane. To hasten the formation of this complex, the antibody and antigen are generally incubated at a temperature of from about 15° to about 30° C. for up to 10 minutes. Preferably, the incubation is carried out at from about 18° to about 25° C. (that is, room temperature) for from 1 to 5 minutes. These mild incubation conditions are in sharp contrast to the 30 minutes at 37° C. described as necessary for adsorption of chlamydial antigen to bare supports in U.S. Pat. No. 4,497,899 (noted above).

After the incubation and within about 10 minutes of the antibody-antigen contact, the bound complex is washed one or more times with a wash solution which generally has a pH of from about 7 to about 12. The solution preferably contains one or more surfactants to aid in separating unbound materials from the bound complex. Particularly useful surfactants are cationic surfactants, as described in copending U.S. Ser. No. 255,924, filed on even date herewith by Pronovost and Gilbert and entitled "Wash Composition Containing a Cationic Surfactant and Its Use in Chlamydial and Gonococcal Determinations."

In the embodiment described above where the chlamydial or gonococcal antibody is labeled, the assay procedure after washing is to detect the label directly or indirectly after addition of the appropriate reagents. This is done relatively quickly after washing the bound complex, that is generally within about 10 minutes, and preferably within about 1 to about 5 minutes. If desired, label detection can be hastened with incubation if the reagents warrant it. The label is then detected using standard equipment and procedures.

In the preferred embodiment, the chlamydial or gonococcal antibody is unlabeled, and after washing the bound complex, it is contacted with an antibody directed to the unlabeled antibody. This second antibody (that is, an anti-antibody) is appropriately labeled with any of the labels described above. The antibody can be monoclonal or polyclonal and either purchased or prepared using known techniques. In a chlamydial assay, the anti-antibody is preferably a polyclonal antibody which is reactive with either of the lipopolysaccharide or major outer membrane protein antibodies.

After this contact, the resulting antigen-antibody-antibody complex which is bound to the coated membrane is incubated for up to about 10 minutes at a temperature of from about 15° to about 30° C., and preferably for about 1 to about 5 minutes at from 18° to 25° C.

Further washing is carried out to remove uncomplexed materials, and suitable enzyme substrates or other needed reagents are added to provide a detectable species. The bound antigen-antibody-labeled antibody complex is then detected on the membrane using standard radiometric, colorimetric, fluorescent or other detection techniques.

The diagnostic test kit of the present invention comprises the coated membrane described herein and one or more other component compositions, solutions or devices for carrying out the assay. For instance, it generally includes a reagent composition comprising an antibody (labeled or unlabeled) to a chlamydial or gonococcal antigen. Additional optional materials in the kit include wash solutions, dye-providing compositions, labeled anti-antibody compositions, extraction compositions, extraction devices, swabs or other specimen collecting means, disposable test devices and others known to one skilled in the art. Preferably, the kit includes the coated membrane mounted as part of a disposable test device.

The following example is provided to illustrate, but not limit the scope of, the present invention.

EXAMPLE

Comparison of Charged and Surfactant-Coated Uncharged Microporous Membranes in Chlamydial Determinations This example illustrates the practice of ths present invention and compares it to the invention described and claimed in U.S. Ser. No. 255,923 of Pronovost (noted above) wherein a positively charged microporous membrane is used in the assay.

Materials Used

The following materials and compositions were used in the assay.

The microporous membrane used in the practice of this invention was an uncharged nylon 66 membrane purchased from Pall Corp. as Biodyne TM A and which was coated with about 50 mg/m$^2$ of Zonyl TM FSN nonionic surfactant (DuPont). The Control charged membrane (according to U.S. Ser. No. 255,923, noted above) was purchased from Pall Corp. as Biodyne TM B. These membranes were mounted in each of the three test wells of disposable test devices like those described in U.S. Ser. No. 98,248 (noted above).

Specimens for testing were obtained from female patients using endocervical swabs. The specimens contained large amounts of whole blood or mucus, and were also tested using standard culture techniques. Each specimen was tested using separate test devices having the Control membrane or the surfactant-coated membrane of the present invention.

An extraction device like those described in U.S. Pat. No. 4,746,614 (noted above) was used to extract chlamydial antigen from the specimens by drying at separate locations on the inside thereof: (1) a coating of Trizma TM (Sigma Chemical) buffer (20 µl of 1.65 molar solution, pH 11.1) and thimerosal preservative (0.01 weight %), and (2) 2-(N-morpholino)ethane sulfonic acid (10 mmolar, 50 µl solution), sodium azide (1.54 mmolar), ethylenediaminetetraacetic acid (5.4 mmolar), 5,5-dimethyl-1,3-cyclohexanedione (21.4 mmolar), dithiothreitol (0.188 molar) and poly(acrylamide)(6.35 weight %).

Composition 1: contained Amideck TM protease (4 µg/ml, 170 units/mg, available form BioProducts Division, Eastman Kodak Co.) in 10 mmolar 2-(N-morpholino)ethane sulfonic acid buffer (pH 6), sodium chloride (50 mmolar), calcium chloride (5 mmolar), 1,2-propanediol (10% w/v) and preservative (0.01 weight %).

Composition 2: contained ethanolamine (0.47 molar), sodium chloride (0.27 molar), preservative (30 mmolar) ethylenediaminetetraacetic acid (50 mmolar), Emcol TM CC-36 cationic surfactant (0.45 weight % from Witco Chemical) and sodium hydroxide (0.66 normal, pH 13.4).

Composition 3: contained hydrogen peroxide (12 weight % in water), diethylenetriaminepentaacetic acid (10 µmolar) and preservative (0.01 weight %).

Composition 4: contained 3-cyclohexylamino-2-hydroxy-1-propanesulfonic acid buffer (0.05 molar, pH 10), Emcol TM CC-9 cationic surfactant (0.75 weight %) and preservative (0.01 weight %).

Composition 5: contained creatine kinase-MB antibody (5 µg/ml), casein (0.01 weight %), Lonzaine TM C amphoteric surfactant (0.01 weight % from Lonza Corp.) and preservative (0.01 weight %) in phosphate buffered saline solution (pH 7.2).

Composition 6: contained chlamydial lipopolysaccharide monoclonal antibodies prepared using standard hybridoma technology and a mouse cell line (4 µg/ml) and the non-antibody components of Composition 5.

Composition 7: contained goat anti-mouse IgG antibodies conjugated to horseradish peroxidase (from BioRad Labs.) (1:700 dilution) in the non-antibody components of Composition 5, along with 4'-hydroxyacetanilide (10 mmolar).

Composition 8: contained 2-(4-hydroxy-3-methoxyphenyl)-4,5-bis(4-methoxyphenyl)imidazole leuco dye (0.008 weight %), poly(vinyl pyrrolidone) (1 weight %), sodium phosphate (10 mmolar, pH 6.8) diethylenetriaminepentaacetic acid (10 μmolar), 4'-hydroxyacetanilide (2 mmolar) and hydrogen peroxide (10 mmolar).

Assay

In performing the assays of each specimen, Composition 1 (7 drops) was added to the extraction device and a patient swab containing each specimen was placed into the device, rotated 5-10 seconds, followed by incubation of the device for 3 minutes at room temperature (18°-25° C.). Composition 2 was then added to the device containing the swab which was rotated again for 5-10 seconds, and incubation was again carried out for 3 minutes at room temperature. Composition 3 was then added, the swab was rotated again followed by a third incubation.

The resulting solution containing extracted lipopolysaccharide antigen was removed from the device using a pipette, and transferred to each well of a disposable test device (4 drops per well), prefiltered. Fluid was allowed to drain through the microporous membranes in the wells. Each well was then washed with Composition 4 (4 drops per well).

Composition 5 (2 drops) was then added to one of the wells of each test device (considered a negative control well). Composition 6 (2 drops) was added to each of the two remaining wells of each device. One of those two wells (considered a positive control well) contained dried chlamydial lipopolysaccharide antigen on the membrane.

The wash step was repeated after fluid drainage, and Composition 7 (2 drops) was added to each well followed by incubation at room temperature for 5 minutes. After a wash step was carried out, Composition 8 (2 drops) was added to each well. After 5 minutes incubation at room temperature, the resulting dye on the membranes of each test device was visually graded on a scale of 0 to 10 (no density to highest density).

It was observed that the test devices having the surfactant-coated, uncharged membrane provided better sensitivity (93.8%) than the Control devices having the charged membrane (73.3%). In addition, the Control devices exhibited poor drainage of fluid due to the large amounts of whole blood and mucus in the specimens, poorer spot quality and higher backgrounds than the devices used in the present invention.

The invention has been described in detail with particular reference to preferred embodiments thereof, but it will be understood that variations and modifications can be effected within the spirit and scope of the invention.

I claim:

1. A method for the determination of a chlamydial or gonococcal antigen comprising:
   A. contacting chlamydial or gonococcal antigen extracted from a specimen suspected of containing chlamydial or gonococcal organisms, respectively, said specimen further containing whole blood, mucus or components thereof, with a surfactant-coated polyamide microporous membrane which is substantially free of any particulate matter, and which has an average pore size of from about 1 to about 10 μmeter, said surfactant coating being present in an amount of at least about 20 mg/m$^2$, said antigen being immobilized on said coated membrane,
   B. within about 10 minutes of said contacting step A, contacting chlamydial or gonococcal antigen immobilized on said coated membrane with chlamydial or gonococcal antibody, respectively, so as to form an immunological complex on said membrane, and
   C. determining the presence of said complex on said membrane as a measure of the presence of chlamydial or gonococcal antigen, respectively, in said specimen.

2. The method of claim 1 wherein said membrane is composed of polyhexamethylene adipamide.

3. The method of claim 1 wherein said membrane is coated with a surfactant in an amount of from about 50 to about 150 mg/m$^2$.

4. The method of claim 3 wherein said surfactant is a nonionic, anionic or amphoteric surfactant.

5. The method of claim 4 wherein said surfactant is nonionic and contains one or more fluorocarbon moieties.

6. The method of claim 1 for the determination of a chlamydial antigen.

7. The method of claim 1 wherein said membrane has an average pore size of about 5 μmeter.

8. The method of claim 1 wherein said chlamydial or gonococcal antibody is enzyme-labeled, and said complex determination is accomplished using a dye-providing composition which comprises a substrate for said enzyme.

9. The method of claim 1 wherein said chlamydial or gonococcal antibody is unlabeled, and said immunological complex is determined using a labeled anti-antibody which is specific for the chlamydial or gonococcal antibody.

10. The method of claim 9 wherein said anti-antibody is labeled with an enzyme, and said complex determination is accomplished using a dye-providing composition which comprises a substrate for said enzyme.

11. The method of claim 10 wherein said enzyme label is peroxidase.

12. The method of claim 1 wherein said microporous membrane is mounted within a test device.

13. A method for the determination of chlamydial or gonococcal organisms comprising:
   A. extracting chlamydial or gonococcal antigen from chlamydial or gonococcal organisms, respectively, in a biological specimen containing whole blood, mucus or components thereof,
   B. contacting said extracted chlamydial or gonococcal antigen with a surfactant-coated polyamide microporous membrane which is substantially free of any particulate matter, and which has an average pore size of from about 1 to about 10 μmeter, said surfactant being present in an amount of at least about 20 mg/m$^2$,
   C. within about 5 minutes of said contacting step B, contacting chlamydial or gonococcal antigen bound to said coated membrane with a reagent composition comprising an unlabeled chlamydial or gonococcal antibody, respectively, so as to form an unlabeled immunological complex on said membrane,
   D. separating unbound materials in said specimen from said bound complex, E. contacting said bound complex with a labeled antibody to said chlamydial or gonococcal antibody so as to form a labeled immunological complex, F. within about 5 minutes of said contacting step E, separating unbound materials from said labeled complex, and G. determining the presence of said labeled complex on said membrane as a measure of the presence of chlamydial or gonococcal organisms, respectively, in said specimen.

14. The method of claim 13 for the determination of chlamydial organisms.

15. A method for the determination of the lippolysaccharide antigen of *C. trachomatis* comprising:

A. extracting lipopolysaccharide antigen from *C. trachomatis* organisms in a biological specimen containing whole blood, mucus or components thereof, B. contacting said extracted antigen with a surfactant-coated nylon microporous membrane which is substantially free of any particulate matter, and which has an average pore size of about 5 $\mu$meter, said surfactant being present in an amount of from about 50 to about 150 mg/m$^2$, C. separating unbound materials from antigen bound to said coated membrane, and contacting said bound antigen with an unlabeled monoclonal antibody directed to said antigen so as to form an unlabeled immunological complex on said membrane, D. incubating for from about 1 to about 5 minutes at room temperature, E. separating uncomplexed materials from said bound complex by washing, F. contacting said bound complex with a peroxidase-labeled antibody to said chlamydial antibody so as to form a labeled complex bound to said membrane, and incubating for up to about 5 minutes at room temperature, G. separating uncomplexed materials from said bound labeled complex by washing, H. adding a dye-providing composition comprising hydrogen peroxide and a leuco dye which is capable of providing a dye in the presence of peroxidase and hydrogen peroxide, and I. determining the amount of said dye on said membrane as a measure of the amount of *C. trachomatis* in said specimen.

16. The method of claim 15 wherein steps B through I are carried out within less than about 30 minutes.

17. The method of claim 15 wherein said membrane is mounted in a disposable test device used for steps B through I.

18. A diagnostic test kit useful for the determination of a chlamydial or gonococcal antigen comprising:

a) a surfactant-coated microporous membrane having an average pore size of from about 1 to about 10 $\mu$meter and which is substantially free of any particulate matter, said surfactant being present in an amount of at least about 20 mg/m$^2$, and b) a reagent composition comprising antibodies to a chlamydial or gonococcal antigen.

19. The kit of claim 18 wherein said surfactant-coated membrane is mounted in a disposable test device.

20. The kit of claim 18 wherein said membrane is prepared from polyhexamethylene adipamide and is coated with a nonionic surfactant having at least one fluorocarbon group.

* * * * *